US010190953B2

(12) United States Patent
Delpy et al.

(10) Patent No.: US 10,190,953 B2
(45) Date of Patent: Jan. 29, 2019

(54) TOMOGRAPHY SAMPLE PREPARATION SYSTEMS AND METHODS WITH IMPROVED SPEED, AUTOMATION, AND RELIABILITY

(71) Applicant: FEI Company, Hillsboro, OR (US)

(72) Inventors: Guillaume Delpy, London (GB); Guillaume Audoit, Bourgoin Jallieu (FR); Laurens Franz Taemsz Kwakman, Saint Ismier (FR); Chad Rue, Hillsboro, OR (US); Jorge Filevich, Portland, OR (US)

( * ) Notice: Subject to any disclaimer, the term of this patent is extended or adjusted under 35 U.S.C. 154(b) by 0 days.

(21) Appl. No.: 15/802,038

(22) Filed: Nov. 2, 2017

(65) Prior Publication Data

US 2018/0143110 A1     May 24, 2018

(30) Foreign Application Priority Data

Nov. 4, 2016 (EP) .................................. 16197390

(51) Int. Cl.
*G01N 1/00*     (2006.01)
*G01N 1/28*     (2006.01)
(Continued)

(52) U.S. Cl.
CPC ............... *G01N 1/286* (2013.01); *G01N 1/06* (2013.01); *G01N 1/28* (2013.01); *H01J 37/08* (2013.01);
(Continued)

(58) Field of Classification Search
CPC .. G01N 1/286; G01N 1/06; G01N 1/28; H01J 37/08; H01J 37/147; H01J 37/3056;
(Continued)

(56) References Cited

U.S. PATENT DOCUMENTS

| 2006/0186336 A1 | 8/2006 | Giannuzzi et al. |
| 2009/0320624 A1 | 12/2009 | Amador |
| 2013/0213945 A1 | 8/2013 | Stegmann |

FOREIGN PATENT DOCUMENTS

| DE | 102011119164 | 5/2013 |
| JP | 2005 233786 A | 9/2005 |
| JP | 2006 220421 A | 8/2006 |

OTHER PUBLICATIONS

Bleuet et al. "SEM-based system for 100nm x-ray tomography or the analysis of porous silicon," Proc. SPIE 9212:92120Z1-92120Z9 (2014).

(Continued)

*Primary Examiner* — Nicole Ippolito
*Assistant Examiner* — Hanway Chang
(74) *Attorney, Agent, or Firm* — Klarquist Sparkman, LLP

(57) ABSTRACT

Sample pillars for x-ray tomography or other tomography scanning are created using an innovative milling strategy on a Plasma-FIB. The strategies are provided in methods, systems, and program products executable to perform the strategies herein. The milling strategy creates an asymmetrical crater around a sample pillar, and provides a single cut cut-free process. Various embodiments may include tuning the ion dose as a function of pixel coordinates along with optimization of the beam scan and crater geometries, drastically reducing the preparation time and significantly improving the overall workflow efficiency. A novel cut-free milling pattern is provided with a crescent shape and optimized dwell-time values.

20 Claims, 13 Drawing Sheets

(51) Int. Cl.
　　*H01J 37/08*　　　(2006.01)
　　*H01J 37/147*　　(2006.01)
　　*G01N 1/06*　　　(2006.01)
　　*H01J 37/305*　　(2006.01)

(52) U.S. Cl.
　　CPC ........ *H01J 37/147* (2013.01); *H01J 37/3056* (2013.01); *H01J 2237/08* (2013.01); *H01J 2237/3114* (2013.01); *H01J 2237/31745* (2013.01)

(58) Field of Classification Search
　　CPC ........... H01J 2237/08; H01J 2237/3114; H01J 2237/31745
　　USPC ................................ 250/492.1, 492.2, 492.3
　　See application file for complete search history.

(56) References Cited

OTHER PUBLICATIONS

Extended European Search Report mailed by the European Patent Office dated May 9, 2017, for EP App. No. 16197390.4.
Sanchez et al. "X-ray μLane diffraction analysis of Cu through-silicon vias: A two-dimensional and three-dimensional study," J. Appl. Phys. 116:163509-1 to 163509-10 (2014).

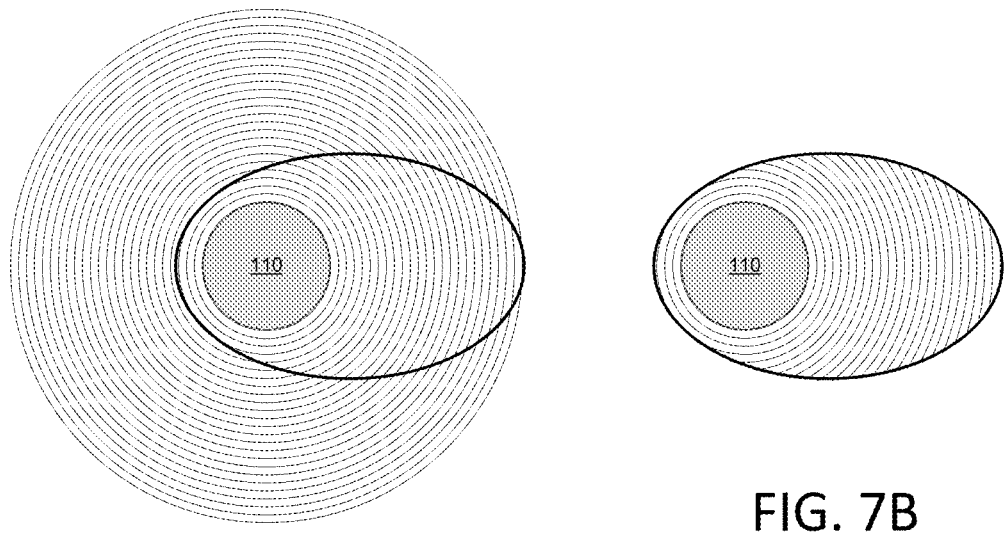
FIG. 7B
FIG. 7A
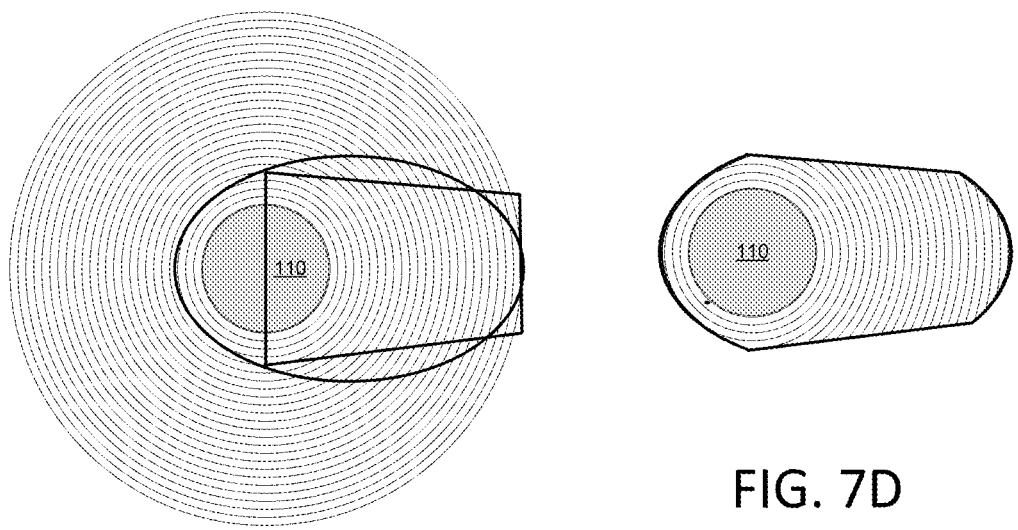
FIG. 7D
FIG. 7C

TOMOGRAPHY SAMPLE PREPARATION SYSTEMS AND METHODS WITH IMPROVED SPEED, AUTOMATION, AND RELIABILITY

CROSS REFERENCE TO RELATED APPLICATION

This application claims priority to European Patent Application No. 16197390.4, filed Nov. 4, 2016, which is incorporated herein by reference.

TECHNICAL FIELD

The present disclosure relates to a process for creating a focused beam sample preparation especially suited for tomography applications such as e.g. X-ray nano CT and Atom Probe Tomography.

BACKGROUND

Recent developments of computed x-ray nano-tomography have shown the potential of this technique for 3D physical characterization and failure analysis of 3D-IC interconnects and other features in semiconductor devices. However, current procedures of preparing samples for tomography by milling and cutting the samples with a focused ion beam (FIB) suffer from extremely long procedure times. Focused ion beam sample preparation for tomography applications, such as, for example, X-ray nano CT and Atom Probe Tomography, is typically time consuming as a lot of material removal is involved and the overall process is not very reliable as the success rate is negatively impacted by the poor control of the sample extraction from its bulk environment.

These are the two main problems encountered with state of the art sample preparation of X-ray tomography samples. FIG. 1A is a cross sectional diagraming showing a prior art concept of preparing and cutting of a cylindrical sample from a bulk sample. FIG. 1B shows two perspective images of a sample pillar created with such a technique, the left image with the sample pillar before extraction from the crater, and the right image showing the sample pillar mounted to a sample holder. Referring to FIG. 1A, depicted is a classical symmetric circular geometry FIB milled crater with a two-sided cut. The cut of a pillar having height h and radius Rint is made at around a 45-degree angle from two sides of a circular crater with an outer radius of Rext. The total depth of the crater, z needs to be at least h+Rint to perform the procedure. Such tomography samples are preferred to be cylindrical because a) the tomography is done over 360° rotation and the sample to X-ray source distance needs to be kept minimal (<1 mm) and b) the X-ray absorption length is constant for all sample rotational positions. Preparation of such samples requires the removal of relatively large material volumes for which a high milling rate Plasma-FIB is used. According to prior procedures, the PFIB (plasma focused-ion beam) based preparation method takes approximately 4.5 hours for a cylindrical sample of approximately 100 um diameter and 100 um height, which is too long to be practical if the goal is to prepare many of such samples and obtain X-ray tomography results within 4-8 hours. Approximately 3 hours are needed for PFIB material removal and the other 1.5 hours are used for the cut free, extraction and transfer of the cylindrical sample to a specific sample holder. The latter extraction steps are slow and most importantly not very reliable due to redeposition of material that frequently causes the samples to be damaged or lost during the extraction step. Hence the overall success rate is rather low and slows the average sample preparation time even further.

Not many labs are currently using a (P)FIB for X-ray tomography samples preparation. If not done by FIB, today, tomography sample preparation is done by polishing, sawing and depositing the samples in capillaries. Such methods are very limited, because these cannot be used for every type of materials and can create artefacts such as cracks and delamination. Moreover, unlike FIB, these methods cannot provide an accurate location of the zone of interest within the sample.

Use of a Gallium FIB can avoid creating such artefacts, but a Gallium FIB has maximum milling rates that are not high enough for fabricating tomography samples with large dimensions on the order of approximately 100 µm. Hence, solutions require the use of focused beams with sufficient energy and flux to arrive at acceptable material removal rates. Therefore, because of their high milling rates, plasma-FIB and pulsed lasers are ideal candidates for this kind of sample preparation. What is needed are fast, efficient and accurate methods to control such tools to produce and scan large tomography samples. What is also needed are techniques to improve reliability of sample cut-free and lift-out methods for tomography samples. Still further, methods are needed to improve automation in the sample generation process.

SUMMARY

Sample pillars for x-ray tomography or other tomography scanning are created using an innovative milling strategy on a Plasma-FIB. The strategies are provided in methods, systems, and program products executable to perform the strategies herein. The milling strategy creates an asymmetrical crater around a sample pillar, and provides a single cut cut-free process. Various embodiments provide several techniques for tuning the ion dose as a function of pixel coordinates along with optimization of the beam scan and crater geometries, drastically reducing the preparation time and significantly improving the overall workflow efficiency. A novel cut-free milling pattern is provided with a crescent shape and optimized dwell-time values.

An object of the disclosure is to ameliorate the problems of excessive milling time and unreliable sample extraction in focused beam sample preparation for tomography applications such as, for example, X-ray nano CT and Atom Probe Tomography. Another object is to provide improved methods for using computed x-ray nano-tomography in a Scanning Electron Microscope for 3D physical characterization and failure analysis of 3D feature such as 3D-IC interconnects. A sample for this purpose, for example, a cylindrically-shaped sample of about 100 µm in diameter and height, is required to be placed on top of a tip or needle shaped sample rod. Other pillar shapes such as rectangles, cones, and needles may be used. Preparation of such samples requires the removal of relatively large material volumes for which a high milling rate Plasma-FIB was used. Still, the preliminary attempts in the industry to produce such samples suffered from lengthy preparation times and poor reliability. Hence, another object of the disclosure is to provide further optimization to improve both the sample preparation time and the success rate to more practical and industrially acceptable levels—the overall X-ray tomography analysis is desired to take less than 4-8 hours. Realizing that the X-ray image acquisition and reconstruction can take up already several hours, the sample preparation for this one example type of samples should not take longer than 1-2 hours, which is significantly shorter than the typical 4.5 hours of prior art techniques.

Various embodiments herein provide methods to create a (cylindrical) sample of user-defined dimensions based on a novel (Plasma-FIB) beam scanning strategy, a specific beam milling pattern to arrive at optimized geometries, and a new sample extraction process that is optimized for the specific geometries, minimizes unwanted re-deposition and has a near 100% sample extraction success rate. To execute the methods herein a software application may be used that executes the complex mathematical calculations and the control algorithms. The methods herein prepare samples in a time that is 2-3 times shorter compared to state-of-the-art methods already used, and have a very high overall success rate. Further, they can be performed with most steps automated, and with minimal operator interventions, allowing unassisted overnight execution.

According to one aspect of the disclosure, a method is provided for creating a tomography sample from a sample substrate, the method including: (a) identifying a target area and underlying target volume of the substrate containing a region of interest; (b) creating a mill pattern based on the target area and a desired sample pillar height and width; (c) with a focused ion beam (FIB) milling a crater asymmetrically positioned around the target area to form a sample pillar containing the target volume. The crater is large enough to allow a single FIB cut at a desired angle from vertical (with respect to the sample pillar orientation) to pass within the crater and cut the sample pillar free from the substrate. The crater is deeper on the side opposite the cutting side to accommodate the opposite end of the single FIB cut to leave the sample pillar detached after the single FIB cut. The crater also has a much smaller gap between the sample and the crater edge on the side opposite the cutting side, to help reduce the amount of material milled. The method next attaches a probe tip of probe to the sample pillar, cuts the pillar free with the single FIB cut at the desired angle, and uses the probe to move the sample pillar to a sample holder.

In some implementations, the crater has an oval shape and the milling includes directing the FIB in a number of adjacent curved lines of FIB dwell positions, and the dwell position dwell times and numbers of repetitions per curved line increase from an outer edge of the crater to an inner edge of the crater. The dwell position dwell times and numbers of repetitions per curved line may be calculated as a function or R using optimized mathematical functions and the user-defined information about targeted sample dimensions (pillar width and pillar height). Linear functions are preferred over constant or quadratic functions. The dwell position dwell times may be further adjusted according to a parabolic function for the dwell time as a function of position on a given circular line on a template or model associated with the respective FIB dwell positions. The curved lines may be selected as line segments by masking an oval or ellipse off from a template pattern including a number of concentric circles, for which linear functions and parabolic functions are calculated, leaving only pixels inside the oval active or used in the milling pattern.

In some embodiments, the desired angle for the single FIB cut may be approximately 60 degrees. According to other embodiments, the desired angle for the single FIB cut is in a range of 55 degrees or more. The milling may be performed automatically according to a pattern automatically generated to control the milling based on the target area and desired sample pillar height and width.

According to some implementations, the crater is milled using a scan pattern including lines of FIB dwell positions wherein the lines have a radial dwell position overlap (OvR) of approximately 80%, and a tangential dwell position overlap (OvT) of approximately 70%. Other implementations may have overlaps that vary within 20% of these overlaps.

According to some implementations, the method further includes creating a cut-free milling pattern with an elliptical distribution of dwell position dwell times across the diameter of the sample pillar, and providing the pattern to control the step of cutting the pillar free. The cut-free milling pattern may have a crescent shape with edges of the crescent shape calculated based on the sample pillar width.

According to some implementations, the FIB is a plasma FIB (PFIB) operated at a high beam current of about 1-2 micro-amps for the milling and cutting operations. Such an arrangement may be employed according to some methods to create a sample pillar that is approximately 100 μm in height and 50 μm in radius, and complete the milling and cutting operations in less than about 2 hours.

According to some implementations, the sample holder is a single-sample needle-shaped holder and the method further includes conducting a series of tomographic data scans on the sample pillar.

In another aspect of the disclosure, similar techniques are employed to create sample specimens with a rectangular shape. In still other aspects, similar techniques are employed to create conical or needle-shaped specimens.

In another aspect of the disclosure, an ion beam system is provided for preparing a sample. The system includes a plasma ion source, an ion beam focusing column, deflection coils, a vacuum chamber, and a movable sample stage positioned in the vacuum chamber and adapted for holding the sample substrate for milling and cutting. The system has a system controller operatively connected to the plasma source, the focusing column, the deflection coils, and the sample stage, the system controller has computer memory storing software program code executable by the system controller for performing the methods set forth herein.

According to another aspect, the disclosure may be embodied as the program code executable for creating the milling patterns and performing the mathematical calculations herein, receiving input from the operator, and executing the methods discussed herein. According to some implementations, the methods herein can reduce PFIB mill time of 100 um tall sample cylinders (with 100 um diameters) to approximately 1 hour, and provide a near 100% success rate for the sample extraction steps. Moreover, as the overall process requires mathematical calculations to obtain the appropriate streamfiles that define the pixel by pixel PFIB milling sequence, a software module is provided according to some embodiments of the disclosure that includes the codes for mathematical algorithms and also enables the automatic execution of the sample preparation process, thereby cutting back on operator time significantly and allowing unattended overnight processing of (multiple) samples that then can be extracted and transferred by an operator assisted sequence afterwards.

According to other aspects of the disclosure, the solutions are provided that include three or more specific choices of geometries and FIB milling conditions from: 1. An elliptical milling crater (deduced from a circular pattern mill with only "active" pixels that are inside the ellipse) that enables a single FIB cut at 60 degrees instead of two FIB cuts at 45 degrees. 2. A Linear function for dwell time and number of loops as function of the radial position during the milling process. 3. A parabolic function for the dwell time as a function of the position on a given circle. 4. Cut the pillar free using crescent cut-free geometry with the exact shape calculated based on a single parameter, the cylinder sample diameter. 5. An elliptical function of the dwell time as a function of the position within the crescent.

The foregoing has outlined rather broadly the features and technical advantages of the present disclosure in order that the detailed description of the disclosure that follows may be better understood. Additional features and advantages of the disclosure will be described hereinafter. It should be appreciated by those skilled in the art that the conception and specific embodiments disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

For a thorough understanding of the present disclosure, and advantages thereof, reference is now made to the following descriptions taken in conjunction with the accompanying drawings, in which:

FIGS. 7A-7D are diagrams showing a milling pattern for a crater being created by masking off a circular template.

DETAILED DESCRIPTION

Methods, apparatus, sample structures, and systems according to various embodiments herein provide methods to create a sample pillar for tomography scanning (or for non-tomography applications, a sample lamella of any suitable lamella shape) having user-defined dimensions based on a novel (Plasma-FIB) beam scanning strategy, a specific beam milling pattern to arrive at optimized geometries, and a new sample extraction process that is optimized for the specific geometries, minimizes unwanted re-deposition and has a near 100% sample extraction success-rate. The techniques herein allow preparing the samples in 2 hours and with a success rate close to 100%.

Figure 1A:
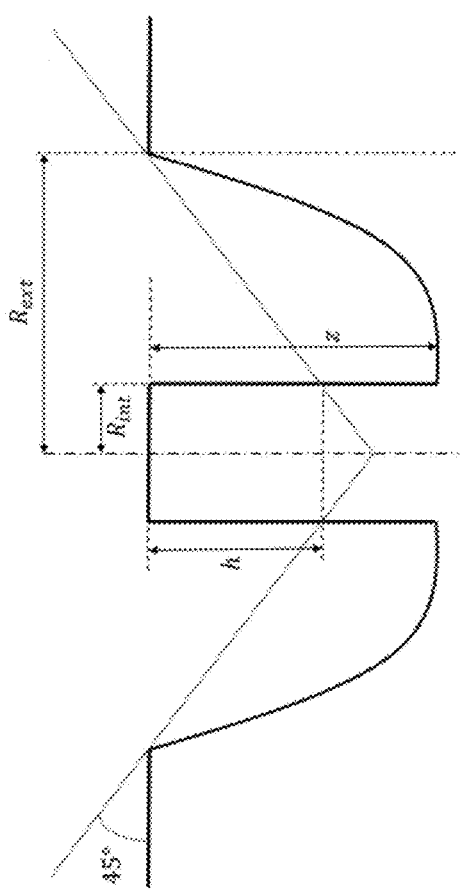
FIG. 1A is a cross sectional diagraming showing a prior art concept of preparing and cutting of a cylindrical sample from a bulk sample.
Figure 1B:
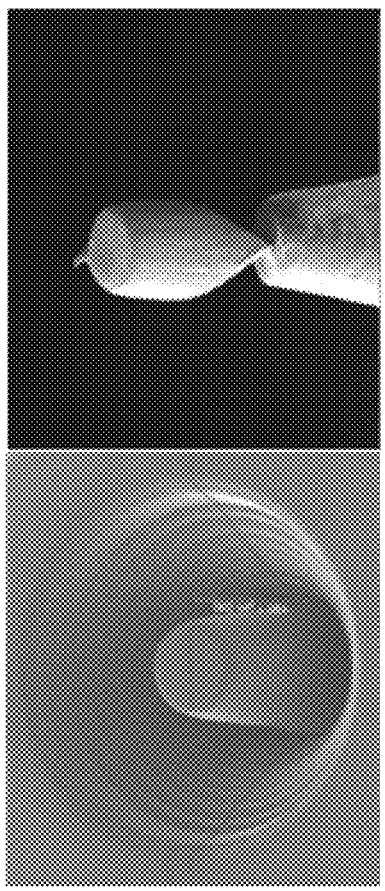
FIG. 1B is a perspective image of a typical crater milled with such a technique.
Figure 2A:
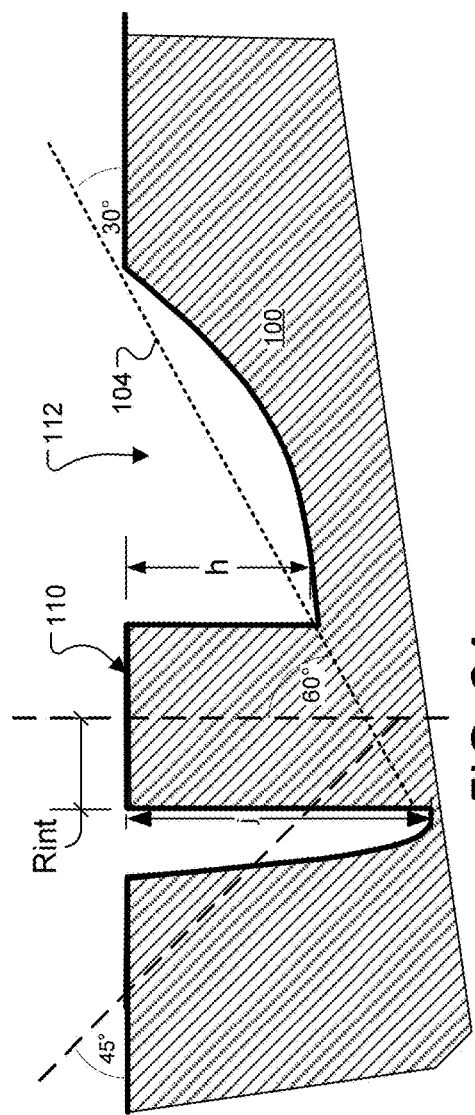
FIGS. 2A-2C are diagrams of a preferred milling geometry, but the crater and sample pillar or lamella shapes may vary.
Figure 2B:
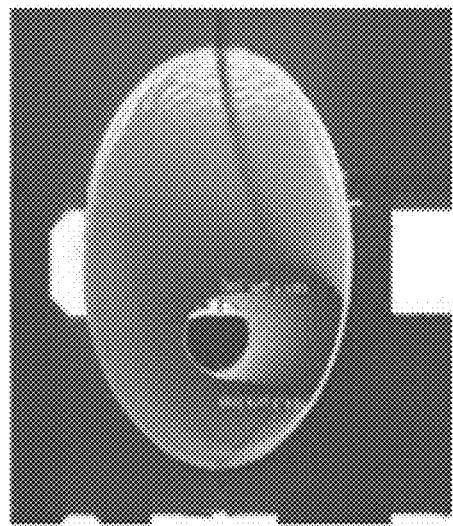
Figure 2C:
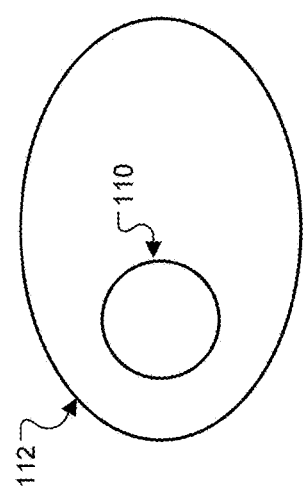
Figure 10:
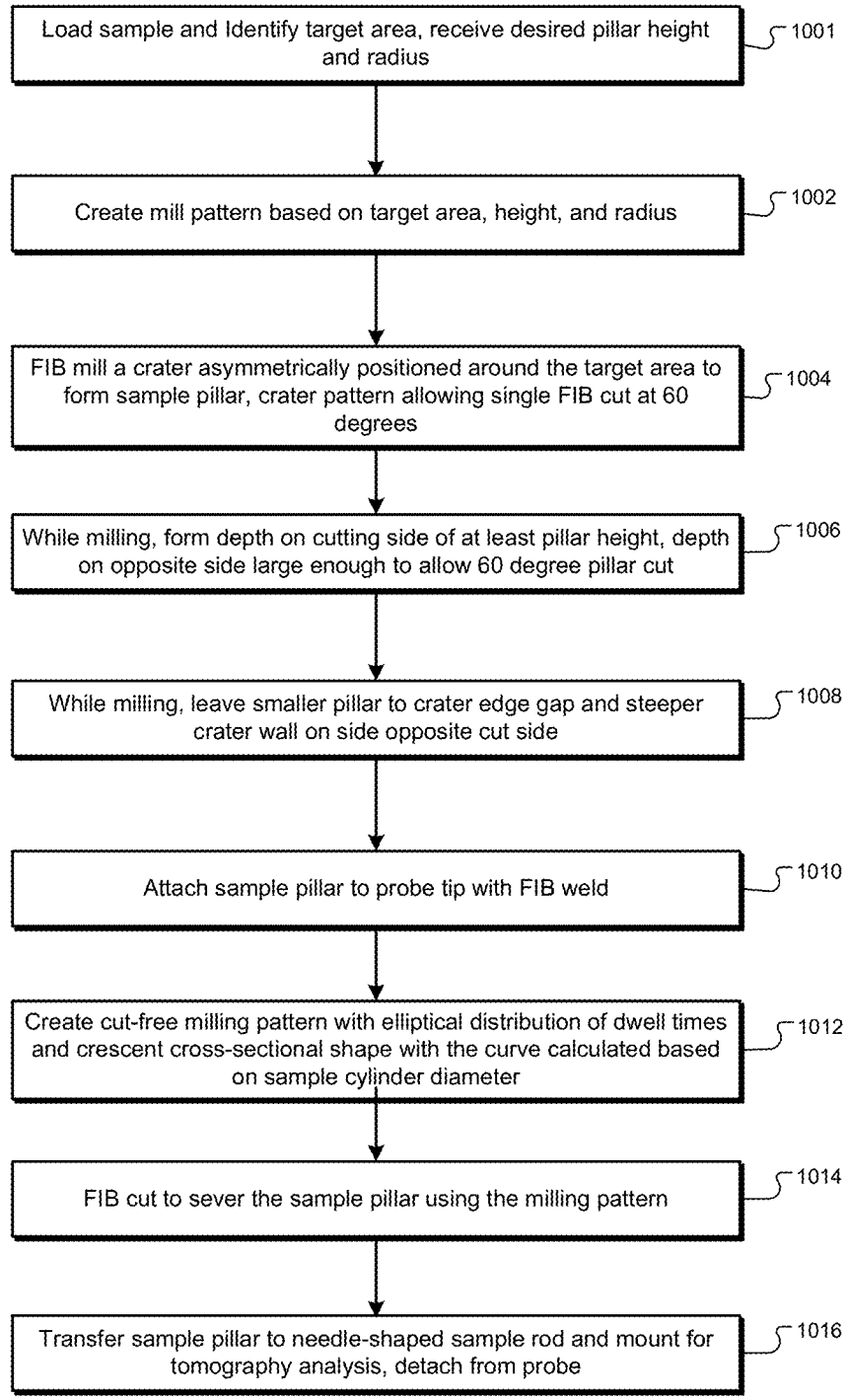
FIG. 10 is a flowchart of an example process for creating a crater using PFIB milling and cutting a sample pillar free.

According to a first aspect of the disclosure, a sample substrate, typically a semiconductor device, is milled to create a tomography sample, which is cut from the substrate and moved to a sample holder such as a sample rod for scanning. FIGS. 2A-C are diagrams of a preferred solution, but the crater and sample pillar or lamella shapes may vary. FIG. 2A is a cross sectional diagram of a portion of semiconductor device substrate 100 showing a preferred crater 112 geometry including a sample pillar 110 after milling is completed. Generally, while the beam milling process can have many variations, an example method of creating the depicted geometry using PFIB milling is shown in the flowchart of FIG. 10. Optimizing other milling parameters will be further described below. The reliability problems discussed above with regard to prior art milling and cutout techniques are exacerbated by using two consecutive cuts on both sides of the pillar. The preferred methods herein lift-out the sample with only one, improved, single FIB cut, and optimize the milling pattern geometry accordingly. To maintain a similar pillar depth (z) the single cut can be done at a different angle, e.g. 60° instead of 45°. This, typically requires more material removal in the periphery, but this can be compensated by applying asymmetric mill patterns. In FIGS. 2A and 2C an elliptical milling pattern with an asymmetric depth profile shows the advantages of this geometry. In total, more material needs to be milled, resulting in a slight increase of the milling time, however, the cutting time is drastically reduced and more important, the success rate of the preparation is now close to 100%. The sample lift-out using an in-situ micro-manipulator (FIG. 8) is now reliable and the cylinder can be easily placed on top of a needle prior to x-ray tomography data acquisition.

Referring to FIGS. 2A-C and the process flowchart of FIG. 10, a method according to this embodiment generally includes, at block 1001, identifying a target area and underlying target volume of the substrate containing a region of interest. The target area is seen in the top view diagram of FIG. 2B, which is commensurate with the top of sample pillar 110. The substrate is loaded on a sample stage of a FIB milling system as further described below. The region of interest is typically a three-dimensional volume underneath the target area containing features of interest such as vertical interconnects between horizontal layers of a semiconductor device. The desired sample pillar shape to be milled is typically cylindrical for tomography applications, but may be conical or other suitable shapes; note in this regard that a cylinder does not necessarily have to have a circular cross-section, though it often will in tomography studies. The target area may be identified by a user by selecting it, or may be identified automatically by recognizing a particular surface feature for a reference point such as a surface fiducial mark (or the outline of a device or device region), and specifying the area as coordinates relative to such a known location as defined in a test procedure. This process block may include referencing CAD data stored on a device in a test system to find the location of features of interest. The desired sample pillar size and shape are generally determined by the test or measurement to be performed, and for the tomography techniques for which the preferred embodiments herein were developed, is usually a vertically oriented cylinder shape with a diameter of 50-100 μm and a height of 50-200 μm. The depicted example is a 100 μm tall cylinder (height h) with a diameter of 100 μm (50 μm radius Rint).

Next, the process at block 1002 creates a mill pattern based on the target area and a desired sample pillar height and radius. The pattern may also be based on other data such as a sample pillar or lamella shape definition. It is noted that the method may also be performed with an operator manually steering the ion beam, however this is not preferred. Next at process block 1004 the process executes the pattern by, with a focused ion beam (FIB), milling a crater 112 asymmetrically positioned around the target area to form a cylindrical sample pillar 110 containing the target volume. As shown in the diagram, the crater is large enough to allow a single FIB cut 104 to pass within the crater and cut sample pillar 110 free from substrate 100 at a desired angle, which in this example is an angle of 60 degrees from vertical (with respect to the sample pillar orientation). While milling, as shown at process block 1006, the crater is formed to have a first depth on a cutting side of the sample pillar of at least the desired sample pillar height (height h). The crater also has a second, larger, depth marked T at the pillar side opposite the cutting side, the second depth j large enough to accommodate the opposite end of the single FIB cut 104 (which can be calculated from the cut angle and pillar diameter plus a desired margin), so that the cut when it is eventually made, cleanly exits the pillar and severs it from the sample substrate 100. The depth j may be calculated to be around 157 μm in this example of using the 60 degrees beam angle and the h and Rint of 100 and 50 μm, respectively. This ratio of minimum required depth on the non-cutting side is constant for a given cutting beam angle, and may be adjusted should the cutting beam angle be varied from 60 degrees. For example, a 55-degree angle would require a smaller depth. It is noted that the cross section of FIG. 2A is shown along the center of the sample pillar and longitudinal center of the crater, but the larger depth must extend far enough around the edges of the crater to allow a flat cut 104 to sever sample pillar 110.

The preferred crater 112 shape is oval as shown in the image of FIG. 2B and diagram of FIG. 2C, and still more preferred is an elliptical oval, asymmetrically positioned with sample pillar 110 offset toward one end of the oval. This is indicated at block 1008, where the milling process leaves a smaller gap from sample pillar 100 to the crater 112 edge on the non-cutting side, allowing less material to be milled generally, and a larger gap on the cutting side from which beam 104 is directed. For the depicted oval version, the gap increases in size around both sides of sample pillar 110 toward the cutting side. The size of the smaller gap is preferably determined by the size of open volume needed to sufficiently reduce redeposition during cutting, and determined also by the minimum gap needed to safely maneuver the pillar out of the crater when attached to a sample probe. Typically, the smaller gap is smaller than a size needed to allow a 45-degree angled cut (with respect to the sample pillar orientation) to pass within the crater at the crater edge opposite the cutting side, as shown in the drawing where the 45-degree angle line that reaches the bottom of the pillar from the sample substrate surface must pass through unmilled substrate. The diagram of FIG. 2A is shown approximately to a relative scale for a preferred solution, with the smaller gap being about 50 μm at the top. In some versions, the size of the gap may be configurable by the user as a percentage of the pillar diameter. A larger gap is generally required for a deeper crater because higher aspect ratios of cuts typically have higher redeposition. Of course, a smaller or larger gap may be used, with a preferred gap being set to the smallest size at which the ion beam employed can reliably (without redeposition that would hamper sample removal) make the cut to the desired depth. Such a width may be saved on the system as a parameter for different beam currents, beam widths, and depths, with the parameters made accessible by the operators and the pattern generation software. The crater 112 is asymmetric in depth as well, with sample pillar 110 formed toward the 'deeper' end of the crater.

Figure 8:
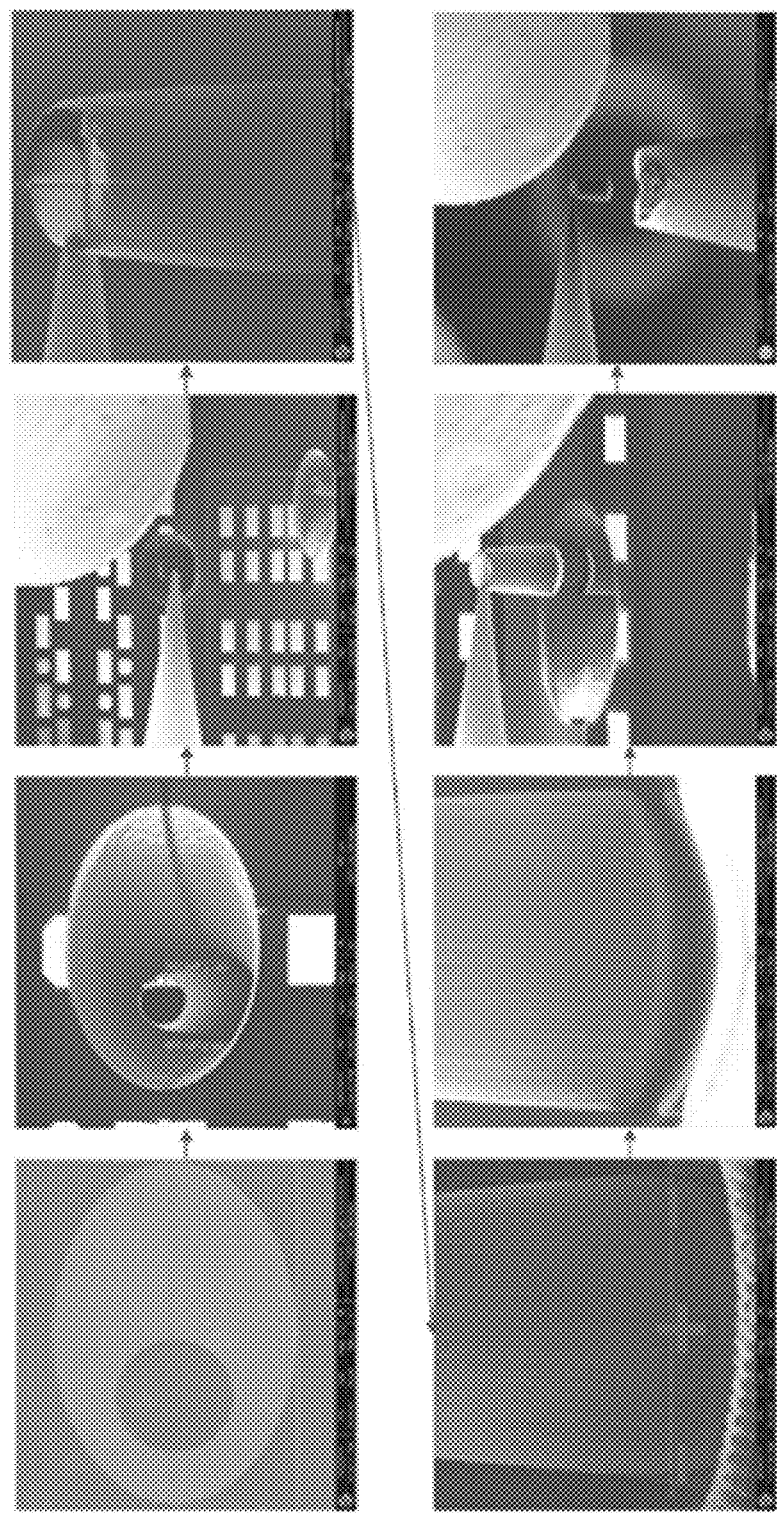
FIG. 8 is a sequence of images showing the preferred total method solution: a cylindrical pillar milling process using asymmetric revolution and an ellipse pattern streamfile followed by a single 60 degrees cut-free process using a crescent pattern streamfile and an elliptical dwell time profile.

Referring now additionally to the series of images shown in FIG. 8, next, the process at block 1010 proceeds by tilting substrate 100 to the appropriate angle and moving a probe 802 adjacent to the sample pillar edge and attaching a probe tip 802 of a probe to sample pillar 110, preferably using an FIB weld attachment (images (c) and (d) of FIG. 8). FIG. 8 is a sequence of images showing the preferred total method solution: a cylindrical pillar milling process using asymmetric revolution (80 minutes) and an ellipse pattern streamfile followed by a single 60 degrees cut-free process (5 minutes) using a crescent pattern streamfile and an elliptical dwell time profile. Additional 20 minutes are needed for weld/de-weld steps.

With sample pillar 110 welded to the probe as depicted in image (c) of FIG. 8, the process at block 1012 creates a milling pattern to perform the cut free operation. The second part of the sample preparation is the cut-free and lift-out of the milled pillar. In the prior art methods, the cut-free step is usually time-consuming and, due to re-deposition and incomplete FIB cuts, irreversible sample damage may occur during the final nano-manipulator lift out step. This non-100% success rate is a serious detractor and needs to be improved to avoid the need of rework and to arrive at acceptable overall sample preparation time efficiencies.

Figure 12:
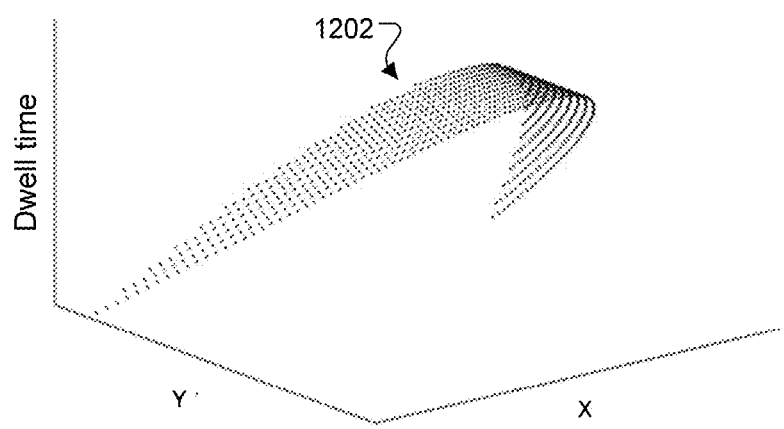
FIG. 12 is a graph of an example cut-free milling pattern.

To solve these problems, the milling pattern is designed for tuning the beam dwell-time in space to optimize local milling speeds and to reduce unwanted local redeposition of sputtered material. Many suitable methods may be employed to create a milling pattern. An example milling pattern is shown in FIG. 12 according to some embodiments of the disclosure. The pattern includes multiple dwell position coordinates (XY) depicted as 1202 on the graph, and their associated dwell times which is shown on the vertical graph axis in this example. The milling pattern may also include a number of repetitions or loops included for each line segment on the pattern with an associated dwell time for each repetition. This can also improve redeposition issues during the cutting process. The provided pattern has many improvements over prior rectangular cutting patterns, and has the advantages of speeding the cutting process and to minimize redeposition during the cut that might tend to leave the sample pillar attached to the substrate with extra deposited material. In this embodiment, a crescent shaped milling pattern 1202 is provided which follows the curve of the sample pillar surface and provides more space in the center to better evacuate matter and reduce redeposition.

This is advantageous because sputtered material evacuated away easily on the extremities of the cut, but it is harder in the center where more material needs to be evacuated through longer diffusion paths. This kind of shape is created mathematically by subtracting the area of a circle that overlaps another circle of dwell positions, shown as dots. The remaining dots correspond to the crescent shaped milling pattern. Next, the process (still at block 1012) applies an elliptical function to the dwell time as a function of the dwell position within the crescent, providing larger dwell times at the thicker portion of the pillar cross section. The combination of the elliptically shaped dwell time profile and the crescent shaped milling pattern has been tested experimentally with a higher reliability than prior art rectangular cutting patterns. The technique combines a new milling geometry (a crescent shape instead of a rectangular box) with a specific dwell-time function to match best the local material removal rate with the exact geometry of the sample to be cut-free and extracted.

Using this cut-free milling pattern, the process continues at block 1014 to cut sample pillar 110 free from substrate 100, by directing the ion beam (preferably the same ion beam employed for milling) to cut across the entire width of the sample pillar, cutting the pillar free with the single FIB cut 104 at approximately 60 degrees. Use of a single cut at this point greatly improves reliability of the process over the prior dual cut methods, as further discussed below. Of course, the cut angle may be increased from 60 degrees by milling away a longer crater (requiring more material to be milled), or decreased by a few degrees, which would require less length along the long dimension of the oval crater but a greater crater depth on the non-cutting side. Generally, what is meant by approximately 60 degrees is the angle can be plus or minus 5 degrees of 60 degrees, but in other versions other angles may be used so long as the required crater shape does not vary so much that so much material is removed that the milling and cutting process time is no longer much less than that when using two 45 degree cuts. For example, another version uses any angle greater than 58 degrees. Still another version uses approximately 55 degrees, or a range of 60+ degrees, 55+ degrees, or 50+ degrees. The cut preferably uses a curved cut-free geometry with respect to varying the dwell times of ion beam dwell locations in the cut, with the curve calculated based on sample cylinder diameter, as further described below.

Figure 9A:
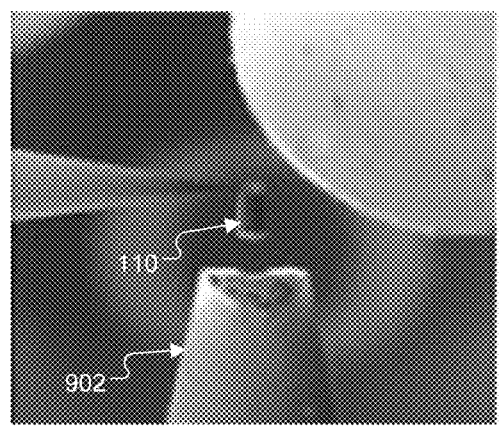
FIG. 9A is an image of a sample pillar being placed atop a sample holder.
Figure 9B:
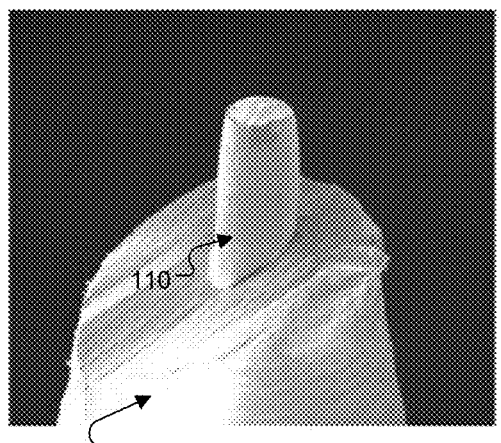
FIG. 9B is an image of a sample pillar mounted atop the sample holder.
Figure 9C:
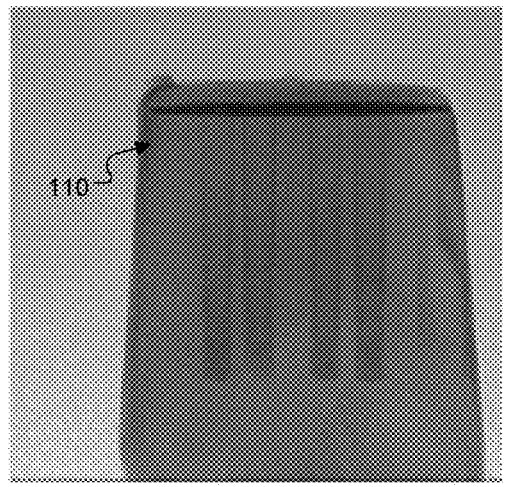
FIG. 9C is an example x-ray image of a sample pillar including 3D interconnects.

Next the method at block 1014 lifts the sample pillar 110 from the crater using probe and transfers it to a sample holder, preferably a sample rod having a needle shape. FIG. 9A shows an image of a sample pillar 110 attached to probe tip 802 being lowered toward a sample holder 902. FIG. 9B is an image of sample pillar 110 after it is mounted to sample holder 902. The sample pillar 110 is mounted to the sample holder typically with an FIB weld, in preparation for a series of tomography scans. FIG. 9C shows a single example image from a tomography scan of sample pillar 110. Sample holder 902 preferably has a top surface slanted to receive the angled bottom surface of sample pillar 110, but other versions may use a flat sample rod and stabilize the sample pillar merely by welding to the sample rod.

Figure 11:
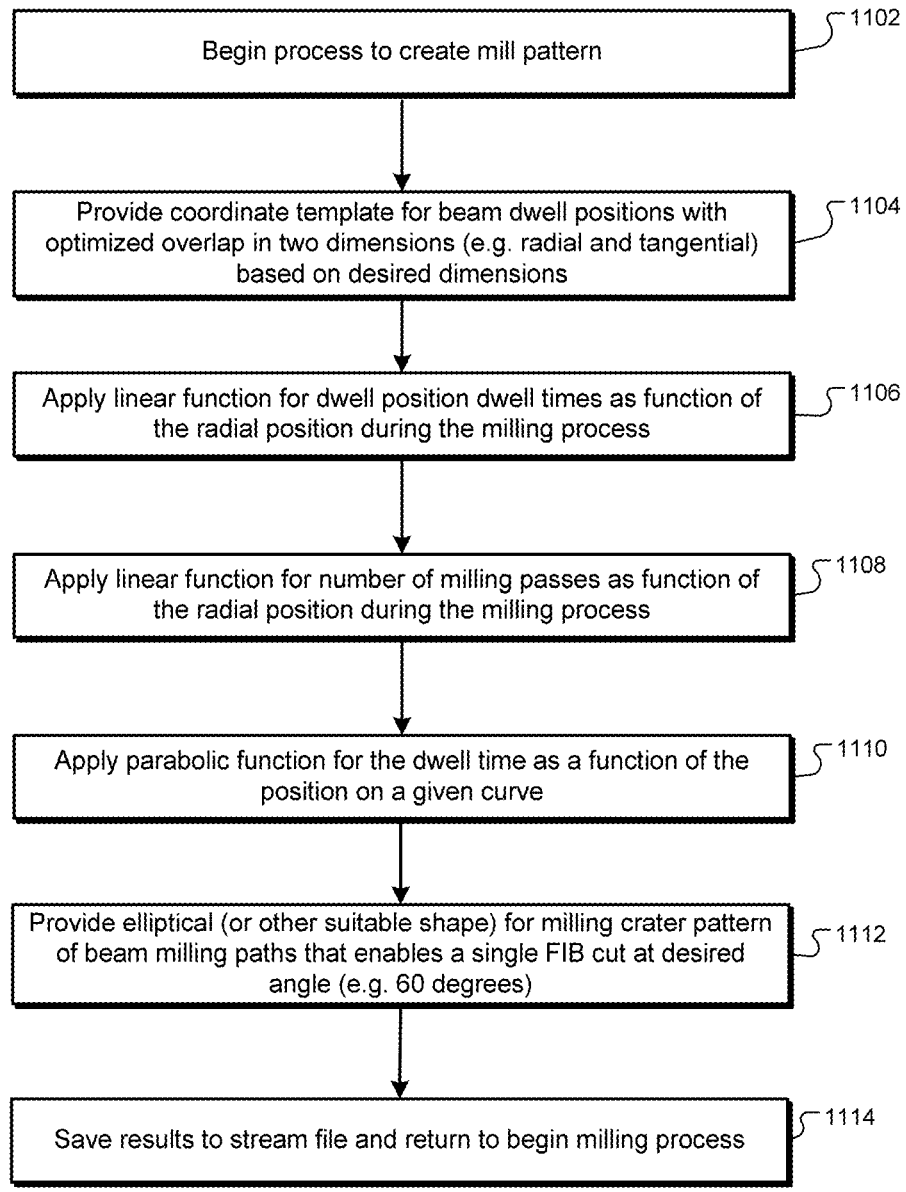
FIG. 11 is a flowchart of an example process for creating and optimizing a milling pattern.

In FIG. 11 a flowchart of a preferred method for generating a milling pattern is presented. FIGS. 3-7 are also referenced below to explain the factors that are optimized in the milling pattern. Generally, to obtain a specific milling geometry, the ion beam is scanned following a two-dimensional pattern that indicates where to strike the surface (XY pixel coordinates), what exact dwell-time to use for each (XY) point, what overlap exists between adjacent beam dwell positions in the scan process, and, finally, how often each of the XY pixel coordinates must be re-visited to complete a scan. The scanning pattern in the preferred version follows a series of circular lines of varying diameter, but does not always traverse a full revolution of the circle (see FIGS. 7B and 7D, for example). For each line the number of loops or scanning repetition passes along the line is defined, as is the dwell time. For a symmetric circular crater, the dwell time is constant for each circle (but varies from one circle to the other). For an asymmetric crater (a preferred solution) the dwell time varies in a quadratic manner along each line.

Figure 4A:
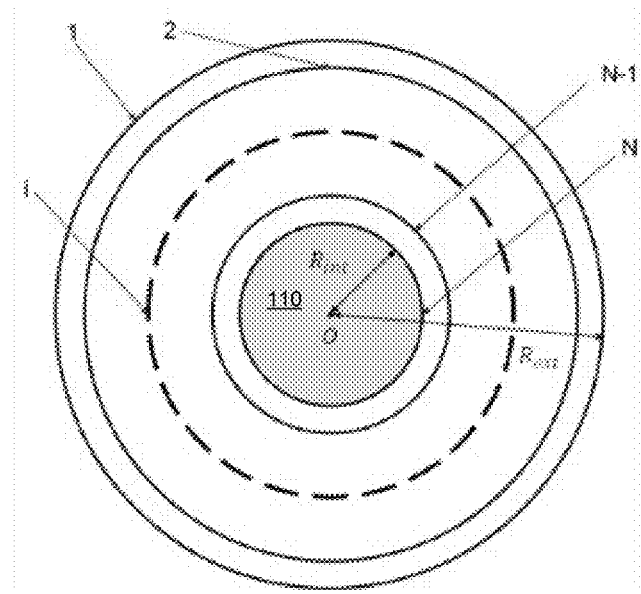
FIGS. 4A and 4B are diagrams showing example circular milling paths and dwell position overlap on such paths.
Figure 4B:
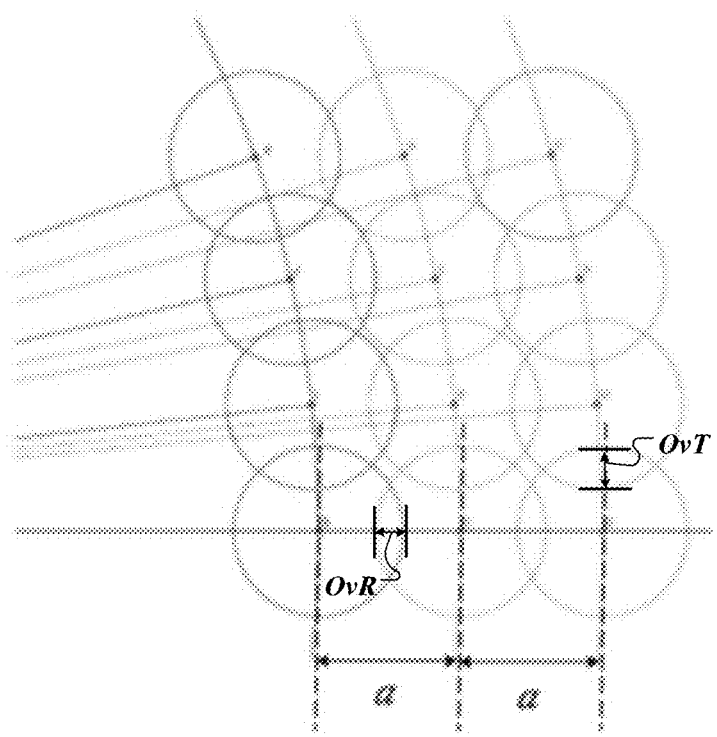
Figure 5:
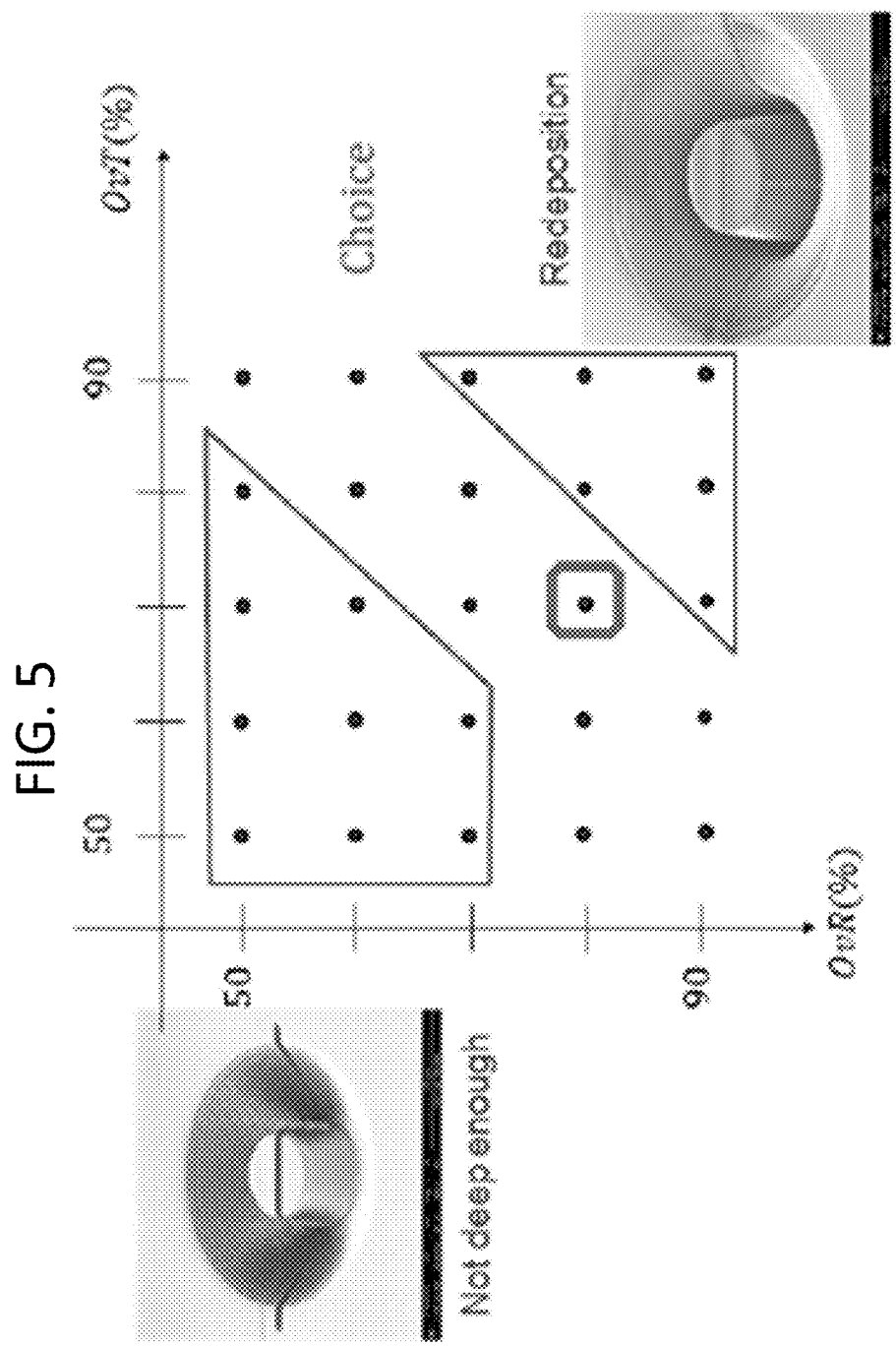
FIG. 5 is an experimental result matrix for experiments on varying dwell position overlaps.

The process to create a mill pattern for a crater around a designated target area begins at block 1102. The pattern may be created based on templates calculated in advance, or some calculations may be done in response to commands by a user to generate a new process for a specified size and shape of sample pillar. For example, a pillar radius of 50 µm and pillar height of 200 µm may be requested at a location to encapsulate a target feature inside the pillar for examination. In some versions, a particular feature may be designated and the system software will begin the designated process by using CAD data stored on the system to look up the three-dimensional size and location of the feature to be examined, and based on this data select one of a number of available sample pillar sizes for which to create a mill pattern. Next at block 1104, the process provides a set of coordinates for beam dwell positions around the target location. The coordinates are preferably optimized to provide a desired dwell position overlap in two dimensions. With reference to FIGS. 4A-4B, an example coordinate set is created with a circular milling pattern including a number N of circular beam milling paths, in which the outer milling path is 1 and the final, inner milling path around the sample pillar 110 is path N. Other geometries may be used such as a square grid of milling locations. As shown in FIG. 4B, the circular paths will have a radial overlap (OvR) between the depicted circle beam dwell locations on adjacent circles, and a tangential overlap (OvT) with adjacent dwell positions on the same circle. It should be noted that OvR is measured at the x-axis as shown in the drawing because it varies around the circumference of a circle because the number of beam dwell locations in each circle is different (n(i)), causing a drift larger and smaller of the OvR. The dwell location patterns are designed to line up locations along the x-axis, allowing a constant reference point for measuring and optimizing OvR there. The present inventors conducted experiments to study the effects of the tangent (OvT) and radial (OvR) overlap, providing a matrix of 25 experiments with OvT and OvR varying from 50% to 90%. A result matrix is shown in the diagram of FIG. 5. For low overlaps the milling rate is not high enough and for high overlaps there is a lot of re-deposition. From these results, the preferred design was selected to be that OvT=70% and OvR=80% values provide optimized results with highest pillars and a practical profile for the subsequent cut and extract steps. Of course, other conditions such as substrate, beam characteristics, or process gas may vary such selection.

With these target values, the circular beam scan paths depicted in FIG. 4A are adjusted in size and dwell position coordinates along the paths to provide a set of dwell position coordinates that yield the desired overlaps for the system beam size. The other parameters are, in the best-optimized embodiments, tuned according to these mathematical calculations of XY pixel coordinates from predefined radial and tangent beam overlaps. These coordinates are typically stored as a set of coordinates for a given range of sample sizes, which is applied as a basis upon which the remainder of the process is conducted.

Figure 3:
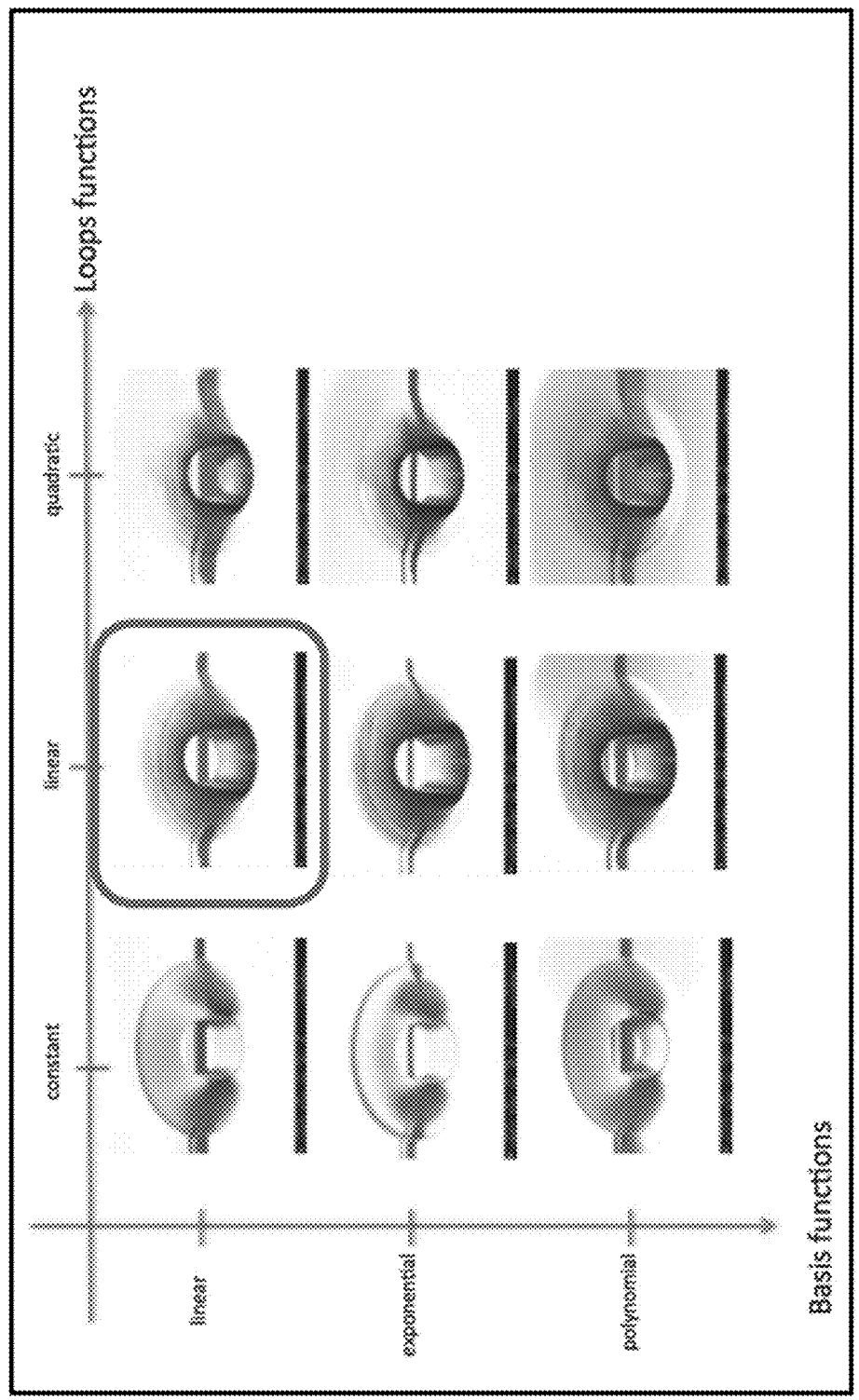
FIG. 3 shows an experimental result matrix, containing images of circular craters created by varying the function type applied to the number of loops and the dwell time basis function.

Referring again to FIG. 11, with the coordinates defined for beam dwell positions, the process next provides the parameters for the depth of the crater with the next three steps. At block 1106 next optimizes the FIB dwell time for each dwell location by applying a linear function for dwell time as function of the radial position during the milling process. The linear function provided is a downward sloping line as R increases, providing generally a shallower crater as R increases. This basis function for setting the dwell times was chosen experimentally along with the function applied at process block 1108, which defines the number of loops (repeated passes along the line or line segment) as function of the radial position during the milling process. FIG. 3 shows an experimental result matrix, containing images of circular craters created by varying the function type applied to the number of loops and the dwell time (=basis) function. The resulting milled profiles are shown for the nine experimental conditions after one hour milling. The main idea here is to combine two effects as the beam scans a circle closer to the pillar, that is, increasing the dwell-time $Dt=Dt(i)$ and increasing the number of loops $Nl=Nl(i)$ per circle. It should be noted that the local material removal depends on the total dose which is the product of $Dt(i)*Nl(i)$, and the amount of redeposition that depends on the dwell time $Dt(i)$ but also on the local crater geometry that is formed in milling steps 1 to $(i-1)$. The effect of varying the dwell time from one circle to another was tested for linear, exponential and polynomial functions. The effect of varying the number of loops per circle line from one circle to another was tested for constant, linear and quadratic functions. The actual number of loops and the dwell time values will vary based on a wide variety of parameters, but for the sample sizes and beam currents used in experiments herein, typical values for the loop numbers ranged from 1 loop for circle #1 to 35 loops for circle #N, and dwell times ranged from 100 μs to 1 ms.

The milling rate strongly depends on the number of loops. Typically, if $Nl(i)$ is constant the milling rate is not high enough. If $Nl(i)$ varies quadratically the milling rate is high enough but off-set by significant re-deposition and the final crater shape is not suitable as there is not enough open space to realize the final FIB-cut under 45 (or 60) degrees. The selected compromise is to choose a linear increase of the number of loops or passes per line as the radial position moves toward the sample pillar location. These scaled dwell time $Dt(i)$ and loop count $Nl(i)$ are saved for each pixel (dwell location) in the crater pattern, those outside the crater pattern are not used and do not need to be calculated.

The dwell time and number of loops (passes or repetitions) per circle are calculated using optimized (in this case, linear) mathematical functions $Fd(r)$ and $Fl(r)$ and the user-defined information about the targeted sample dimensions (cylinder diameter and cylinder height).

Figure 6A:
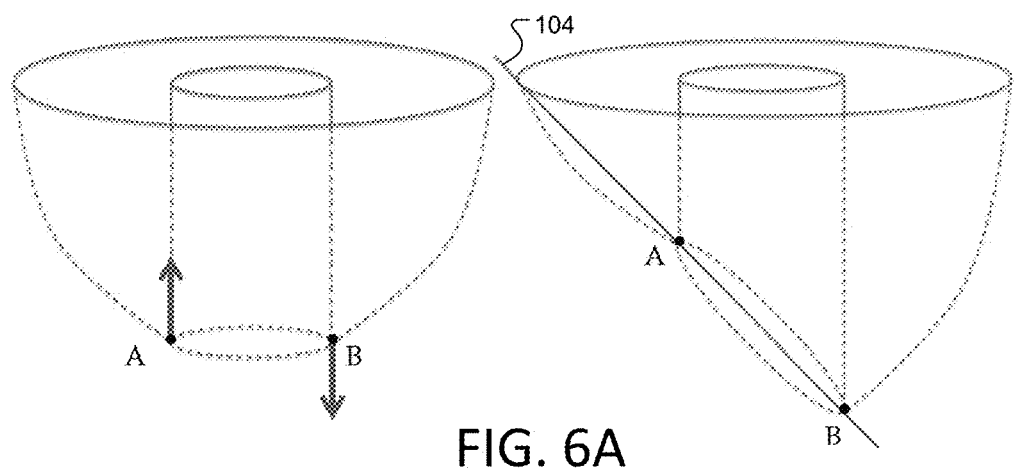
FIGS. 6A and 6B show diagrams of a method of varying milling depth in a crater.
Figure 6B:
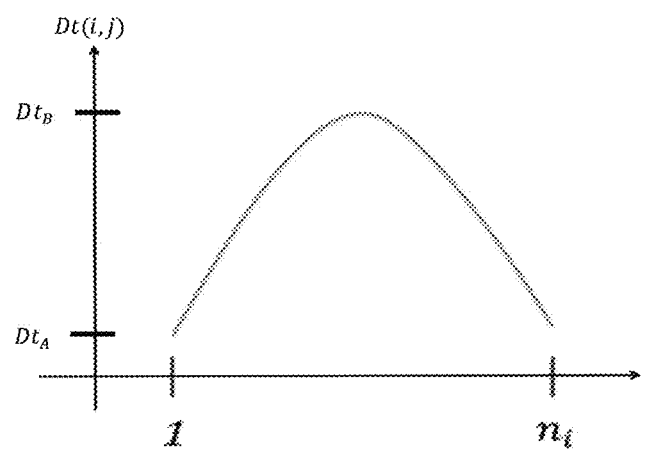

Next at block 1110, the process modifies the calculated dwell time values according to a parabolic function for the dwell time as a function of the position on a given circle. This is done to create the asymmetry in depth discussed above in the preferred versions so that a single cut can be used at the cut-free stage of the process. FIGS. 6A-6B depict this effect with a simple circular crater.

To obtain this kind of shape, the process employs the starting concentric circle pattern template and changes the dwell-time configuration for those points that are included in the current crater pattern. Consider one circle i containing $n_i$ dots indexed with letter j starting at the point desired to be aligned with the cut center. In the previous pattern, dwell-time was constant around a given circle or circle segment $Di(i, j)=Dt(i)$. To obtain the kind of asymmetric shape depicted in FIG. 6A (right hand side) in order to allow a single cut 104 to free the pillar, the dwell times must be increased on the side labelled B to create a deeper crater on that side, and decreased on the side labelled A to make that side relatively shallower. To accomplish this, the process uses a quadratic form as depicted in FIG. 6B, applying it to the dwell positions around the circle. As can be seen in FIG. 6B, the dwell times increase as the circle is traversed from point A to point B, and then decrease again as the circle is traversed fully around to point A. The parabolic curve provides for a smoothly transitioning crater that helps to minimize redeposition in the milling process. Preferably, suitable constants are chosen for the $D(t)$ values at points A and B, and a suitable $2^{nd}$ degree polynomial fitted to the end values. The result is applied to each circle in the basic circle pattern, and these dwell time scaling values may be saved in advance for different pillar depths and diameters, or calculated in response to user inputs. Next, those dwell positions actually used in the current crater pattern are adjusted (scaled) according to the result and saved in to the current pattern. As discussed above, the calculations may in some cases be conducted in advance for a number of cases available for selection by the user when configuring a set of tests to run.

Next at process block 1112, the process provides the final two-dimensional milling paths to create the shape of the crater by masking a desired shape over the optimized set of scanning paths and dwell locations provided above. The preferred version provides an elliptical milling crater (masked from a circular pattern mill with only "active" pixels that are inside the ellipse) that enables a single FIB cut at 60 degrees instead of two FIB cuts at 45 degrees as done in prior systems. Such a masking process is depicted in the diagrams of FIGS. 7A and 7B, where the desired elliptical shape is shown masked over the optimized coordinate set definition to create the crater design shown in FIG. 7B. While the diagrams shown only the milling paths as the circular lines, the dwell position coordinates are included in the masking process. Typically, an actual milling pattern will contain many more lines than shown on the drawing, and may include hundreds of lines obviously depending on the size of the crater and the beam diameter, and the geometry of the scan pattern selected. Further, while the elliptical crater of FIG. 7B is preferred, other crater shapes may be used. For example, FIGS. 7C and 7D show a similar scan path creation process using an intersect of two shapes, an ellipse and a trapezoid. The resulting shape mills slightly less area, and slightly less material, than the elliptical crater but may not be suitable for all conditions. As discussed above, the shape is asymmetrically placed around the target location 110 to provide for a single cut process with minimal extraneous milling. Most of the milling paths inside the depicted shape are now segments of a circle, but other versions may use straight lines or other types of curves or combinations of different lines following the principles herein. Those circular milling paths closest to the crater are retained as full circles in the versions of FIGS. 7B and 7D. The segments retain all of their dwell positions and their optimized XY coordinates already provided. While the methodology of creating the crater milling patterns is described herein, the process may create these in advance and select an appropriate saved pattern for a desired target area, then apply that pattern to the desired location by calculating coordinates relative to the target area.

Next at block 1114, the process saves the results of these optimization steps to a stream file to be accessed for controlling the ion beam when the milling is conducted. It should be noted that these several optimization parameters employed together provide a cumulative effect achieving much reduction in milling time. These factors may also be employed in any suitable sub-combination to optimize milling procedures with different requirements. Further, while a presently preferred method is given to optimize the process with respect to these parameters, other parametric models may be used and other optimization techniques may be used to achieve similar results. Other, simpler, optimization processes may be used to improve a milling pattern to achieve the asymmetrical designs described herein, with a loss of speed as compared to the techniques herein but still achieve the desired result of a fast and reliable, single-cut extraction process for tomography sample pillars.

It should be noted that the use of multiple repetitions along each milling path provides further optimization over a single pass with longer dwell times delivering the total ion dose in one pass. This is because, while the local FIB material removal is proportional to the ion dose (total number of ions per unit area), it also depends on the ion incidence angle, with glancing angles generally having a higher mill rate. But the material removal is also off-set by the material redeposition that occurs and that is more pronounced in confined high aspect ratio structures. Balancing of both effects and optimization of the local net material removal is employed herein by using multiple passes, where the first pass creates a small trench with slanted walls, which then receive the next pass at a glancing angle with the effect of increasing the mill rate for those portions of the beam dwell position. Redeposition during these next passes is much less in this trench than it would be in the deep holes that are formed if the ion beam dwells at each dwell position very long, and, therefore, multiple passes allow to take maximum benefit of the aforementioned increased mill rates. This effect is quite strong on the milling rate. Typically, for silicon, the milling rate increases by a factor 6-8 when milling at 80° (glancing) instead of 0° (perpendicular). For a combined optimization effect of the overall milling time of the structure, the techniques herein tune both the ion dose in space and the beam scanning strategy to define where more material needs to be removed and to optimize the local milling rate, respectively.

Figure 13:
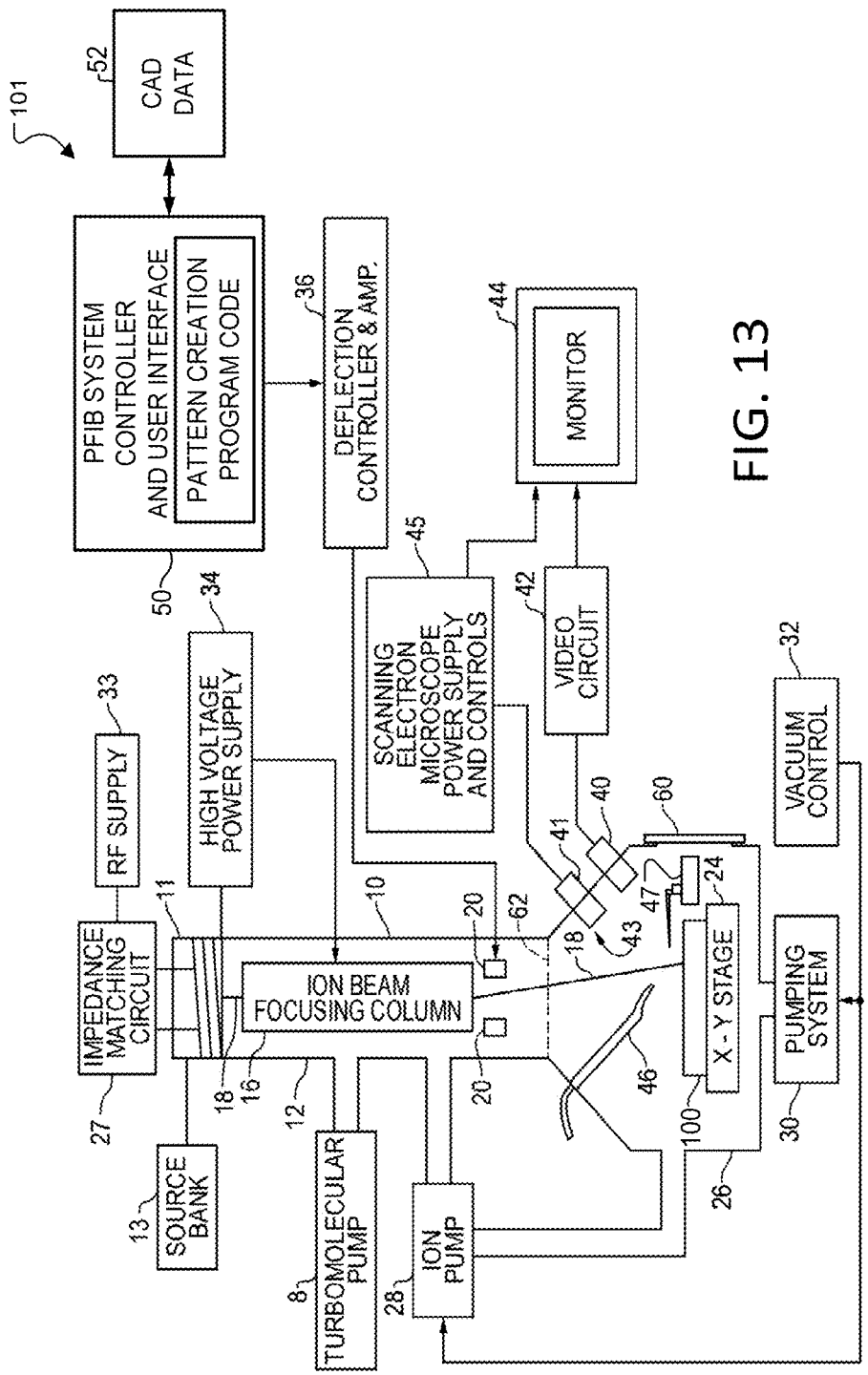
FIG. 13 is a system diagram of an example PFIB system.

The disclosure may also be embodied in a FIB or PFIB system, programmed to perform various embodiments of the processes (methods) exemplified above. Many suitable FIB and PFIB devices may be used, along with dual beam systems and combined pulsed laser and FIB systems. FIG. 13 shows a diagram of an example embodiment of a focused ion beam system including programming to conduct the methods herein. The depicted system 101 includes an evacuated envelope 10 in which is located a plasma ion source 11 including a plasma chamber with a surrounding RF antenna with RF supply 33, and impedance matching circuit 27 to transfer power to the antenna, this PFIB source providing a dense plasma for ion beam focusing column 16. Connected to the plasma source 11 is a bank of sources 13 to provide different ionizable gases for ionization. Ion beam 18 passes from plasma source 11 through column 16 and between electrostatic deflection mechanism 20 toward specimen 22, which comprises, for example, a semiconductor device positioned on movable and tiltable X-Y stage 24 within lower chamber 26.

A turbo-molecular pump 8 is employed for evacuating the source and maintaining high vacuum in the upper column optics region. The vacuum system provides within lower chamber 26 a vacuum of typically between approximately $1 \times 10^{-7}$ Torr ($1.3 \times 10^{-7}$ mbar) and $5 \times 10^{-4}$ Torr ($6.5 \times 10^{-4}$ mbar) with nominally 10 mTorr ($1.3 \times 10^{-3}$ mbar) in the plasma source and $<1 \times 10^{-6}$ Torr ($1.3 \times 10^{-6}$ mbar) in the column optics chamber.

High voltage power supply 34 may be connected to electrodes of plasma source 11 as well as to electrodes in focusing column 16 for forming an approximately 0.1 keV to 50 keV ion beam 18 and directing the same downward. RF power supply 33 and impedance matching circuit 27 is also provided to energize a coil of plasma ion source 11, as described above. Any other suitable known power supply or plasma chamber arrangement may be used. Deflection controller and amplifier 36, operated in accordance with a prescribed pattern provided by pattern generator 38, is coupled to deflection plates 20 whereby beam 18 may be controlled to trace out a corresponding pattern on the upper surface of specimen 22. In some systems, the deflection plates are placed before the final lens, as is well known in the art.

The beam from ion plasma source 11 is brought to a focus at specimen 22 for either modifying (milling) or imaging the surface 22. A charged particle multiplier 40 used for detecting secondary ion or electron emission for imaging is connected to video circuit 42, the latter supplying drive for video monitor 44 also receiving deflection signals from controller 36. A scanning electron microscope 41, along with its power supply and controls 45, are optionally provided with the PFIB system 101. A gas injection nozzle 46 may be provided to inject process gasses near the sample surface. A sample manipulator probe 47, such as a micromanipulator, is provided in the chamber to remove the cut-free sample pillars and transfer them to a sample holder. The holder may be placed into the chamber through portal 60, and removed when a sample is loaded and to be transferred to a tomography system for examination.

Signals applied to deflection controller and amplifier 36, cause the focused ion beam to move within a target area to be imaged or milled according to a pattern controlled by system controller 50. The system controller 50 may be one or more computer systems providing a user interface and processors for executing control algorithms for the various depicted parts of the system. These controls are known in the art and will not be further described here. Relating to the present disclosure, the system controller 50 includes computer memory (tangible, non-transitory memory) storing program code for creating and executing the milling patterns and overall methods (workflows) described herein. As discussed above, the methods according to various embodiments, such as the example methods described with respect to FIGS. 10 and 11, may be executed automatically by the system controller after being configured by an operator through the user interface of system controller 50, or remotely through a network interface. System controller 50 may also connect to a CAD data server or data store 52 in order to access detailed design data for semiconductor devices under test, such as the size and position of features of interest specified by an operator. Further, the system 101 may be connected via network to a larger test system controller that helps to automate sample processing.

Emissions from each sample point are collected by charged particle multiplier 40 to create an image that is displayed on video monitor 44 by way of video circuit 42.

Focusing optics in column 16 may comprise mechanisms known in the art for focusing or methods to be developed in the future. For example, two cylindrically symmetric electrostatic lenses can be implemented to produce a de-magnified image of the round virtual source. Further, embodiments can provide beam currents from about a few pico-amperes to about several micro-amperes.

While a PFIB system is described, this is not limiting and the techniques described herein may be employed with other FIB systems. Further, the disclosure may also be embodied as the program code executable by system controller 50 (in jurisdictions allowing protection of software inventions in this manner), for creating the milling patterns and performing the mathematical calculations herein, receiving input from the operator, and executing the methods discussed herein. What may also be embodied is the methodology herein packaged in a software program that does all the mathematics to calculate the FIB positions, i.e. to calculate exact r, phi positions that correspond with a given tangent and radial overlap value and that moreover calculates the exact dwell-time and number of loops per radius based on just a few user inputs that are strictly limited to the geometrical information of the desired pillar dimensions (radius and depth).

General Considerations

The combination of techniques herein provides a highly optimized, preferred solution and is made after a comprehensive study of the various factors that influence the milling and cut-free characteristics. The new methods are also attractive for other sample preparation processes: multiple atom probe or TEM tomography samples can be prepared in a fast and automated manner using the single-cut process described herein, and then manually finished and extracted by an operator afterwards. Altogether, the disclosure improves sample preparation in terms of speed and overall success rate and allows a system to do this in an automated way.

The control of the PFIB dwell-time in space opens a field of new possibilities. The innovation, proposed to increase the material removal speed, is an optimization process based on a specific choice of number of loops and dwell time and overlap as a function of the FIB dwell position inside a crater pattern. Related optimization procedures are used in different milling patterns (rectangular mills for TEM prep). However, in the proposed innovation the optimized values for dwell time and number of loops are obtained from mathematical functions that are found to be best choices.

The foregoing has outlined rather broadly the features and technical advantages of the present disclosure in order that the detailed description of the disclosure that follows may be better understood. Additional features and advantages of the disclosure will be described hereinafter. It should be appreciated by those skilled in the art that the conception and specific embodiments disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims.

Although the present disclosure and its advantages have been described in detail, it should be understood that various changes, substitutions and alterations can be made herein without departing from the spirit and scope of the disclosure as defined by the appended claims. The combinations of features described herein should not be interpreted to be limiting, and the features herein may be used in any working combination or sub-combination according to the disclosure. This description should therefore be interpreted as providing written support, under U.S. patent law and any relevant foreign patent laws, for any working combination or some sub-combination of the features herein.

Moreover, the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include such processes, machines, manufacture, compositions of matter, means, methods, or steps.

We claim:
1. A method for creating a tomography sample from a sample substrate, comprising:
   (a) identifying a target area and underlying target volume of a substrate containing a region of interest;
   (b) creating a mill pattern based on the target area and a desired sample pillar height and width;
   (c) milling a crater asymmetrically positioned around the identified target area to form a sample pillar containing a target volume using a focused ion beam (FIB), (i) the crater large enough to allow a single FIB cut at a desired angle from vertical with respect to the sample pillar orientation to pass within the crater and cut the sample pillar free from the substrate, (ii) the crater having a first depth on a cutting side of the sample pillar of at least the desired sample pillar height and a second, larger, depth opposite the cutting side, the second depth large enough to accommodate the opposite end of the single FIB cut to leave the sample pillar detached after the single FIB cut, (iii) the crater having a first gap between the sample pillar and a crater edge on the cutting side and a second gap, substantially smaller than the first gap, opposite the cutting side;
   (d) attaching a probe tip of a probe to the sample pillar;
   (e) cutting the sample pillar free with the single FIB cut at the desired angle; and
   (f) using the probe to move the sample pillar to a sample holder.

2. The method of claim 1, wherein the crater has an oval shape and the milling includes directing the FIB in a number of adjacent curved lines of FIB dwell positions, and wherein dwell position dwell times and numbers of repetitions per curved line increase from an outer edge of the crater to an inner edge of the crater.

3. The method of claim 2, wherein the dwell position dwell times and numbers of repetitions per curved line are determined using linear mathematical functions and the user-defined information about targeted sample dimensions including at least one of pillar width and pillar height.

4. The method of claim 3, wherein the dwell position dwell times are further adjusted according to a parabolic function for the dwell time as a function of position on a given circular line in a template pattern comprising a number of concentric circles associated with the respective FIB dwell positions.

5. The method of claim 3, wherein the curved lines are selected as line segments from a template pattern comprising a number of concentric circles, for which linear functions and parabolic functions are determined.

6. The method of claim 2, wherein the dwell position dwell times are further adjusted according to a parabolic function for the dwell time as a function of position on a given circular line in a template pattern comprising a number of concentric circles associated with the respective FIB dwell positions.

7. The method of claim 2, wherein the curved lines are selected as line segments from a template pattern comprising a number of concentric circles, for which linear functions and parabolic functions are determined.

8. The method of claim 2, wherein the milling is performed automatically according to a pattern automatically generated to control the milling based on the target area and desired sample pillar height and width.

9. The method of claim 2, further comprising creating a cut-free milling pattern with an elliptical distribution of dwell position dwell times across the width of the sample pillar, and providing the pattern to control the step of cutting the pillar free.

10. The method of claim 2, wherein the FIB is a plasma FIB (PFIB) operated at a high beam current of about 1-2 micro-amps for the milling and the cutting.

11. The method of claim 1, wherein the desired angle for the single FIB cut is approximately 60 degrees.

12. The method of claim 1, wherein the desired angle for the single FIB cut is in a range of 55 degrees or more.

13. The method of claim 1, wherein the milling is performed automatically according to a pattern automatically generated to control the milling based on the target area and desired sample pillar height and width.

14. The method of claim 1, wherein the crater is milled using a scan pattern including lines of FIB dwell positions wherein the lines have a radial dwell position overlap (OvR) of approximately 80%, and a tangential dwell position overlap (OvT) of approximately 70%.

15. The method of claim 1, further comprising creating a cut-free milling pattern with an elliptical distribution of dwell position dwell times across the width of the sample pillar, and providing the pattern to control the step of cutting the pillar free.

16. The method of claim 15, wherein the cut-free milling pattern has a crescent shape with edges of the crescent shape determined based on the sample pillar width.

17. The method of claim 1, wherein the FIB is a plasma FIB (PFIB) operated at a high beam current of about 1-2 micro-amps for the milling and the cutting.

18. The method of claim 17, wherein the sample pillar is approximately 100 μm in height and 50 μm in radius and wherein the milling and the cutting are completed in less than about 2 hours.

19. The method of claim 1, wherein the sample holder is a single-sample needle-shaped holder and the method further comprises conducting a series of tomographic data scans on the sample pillar.

20. An ion beam system for preparing a sample, comprising:
a plasma ion source;
an ion beam focusing column coupled to receive ions from the plasma ion source and produce an ion beam that is directed toward a vacuum chamber;
deflection coils provided toward a lower end of the ion beam focusing column for steering the ion beam;
a movable sample stage positioned in the vacuum chamber and adapted for holding the sample; and
a system controller operatively connected to the plasma source, the ion beam focusing column, the deflection coils, and the movable sample stage, the system controller including a tangible non-transitory memory storing program code executable by the system controller for performing the method of claim 1.

* * * * *